United States Patent
Wainwright et al.

(10) Patent No.: US 11,006,841 B2
(45) Date of Patent: May 18, 2021

(54) SYSTEMS AND METHODS FOR DETECTING STROKES

(71) Applicant: Covidien LP, Mansfield, MA (US)

(72) Inventors: John Wainwright, Foothill Ranch, CA (US); Heather D. Orser, Farmington, MN (US); Eric J. Panken, Edina, MN (US); Timothy J. Denison, Minneapolis, MN (US)

(73) Assignee: Covidien LP, Mansfield, MA (US)

(*) Notice: Subject to any disclaimer, the term of this patent is extended or adjusted under 35 U.S.C. 154(b) by 174 days.

(21) Appl. No.: 16/001,270

(22) Filed: Jun. 6, 2018

(65) Prior Publication Data

US 2018/0353084 A1    Dec. 13, 2018

Related U.S. Application Data

(60) Provisional application No. 62/516,596, filed on Jun. 7, 2017.

(51) Int. Cl.
*A61B 5/00* (2006.01)
*A61B 5/0205* (2006.01)
(Continued)

(52) U.S. Cl.
CPC .......... *A61B 5/0205* (2013.01); *A61B 5/0075* (2013.01); *A61B 5/0077* (2013.01);
(Continued)

(58) Field of Classification Search
CPC ..... A61B 5/02; A61B 5/0205; A61B 5/02405; A61B 5/0476; A61B 5/4076; A61B 5/7275
See application file for complete search history.

(56) References Cited

U.S. PATENT DOCUMENTS

| 4,201,222 A | 5/1980 | Haase |
| 4,907,597 A | 3/1990 | Chamoun |

(Continued)

FOREIGN PATENT DOCUMENTS

| EP | 2319575 B1 | 11/2013 |
| JP | 2014004219 A | 1/2014 |

(Continued)

OTHER PUBLICATIONS

International Search Report and Written Opinion of International Application No. PCT/US2018/036228, dated Sep. 7, 2018, 13 pp.

(Continued)

*Primary Examiner* — Allen Porter
(74) *Attorney, Agent, or Firm* — Shumaker & Sieffert, P.A.

(57) ABSTRACT

A system for detecting strokes includes a sensor device configured to obtain physiological data from a patient, for example brain activity data. A computing device communicatively coupled to the sensor device is configured to receive the physiological data and compare it with reference data. The reference data can be patient data from an opposite brain hemisphere to the hemisphere being interrogated or the reference data can be non-patient data from stroke and normal patient populations. Based on comparison of the physiological data and the reference data, the system indicates whether the patient has suffered a stroke.

20 Claims, 7 Drawing Sheets

(51) Int. Cl.
*A61B 8/00* (2006.01)
*A61B 5/026* (2006.01)
*A61B 6/00* (2006.01)
*A61B 5/245* (2021.01)
*A61B 5/318* (2021.01)
*A61B 5/389* (2021.01)
*A61B 5/01* (2006.01)
*A61B 6/03* (2006.01)
*A61B 5/055* (2006.01)
*A61B 5/024* (2006.01)
*A61B 5/021* (2006.01)
*A61B 5/08* (2006.01)
*A61B 5/0533* (2021.01)
*A61B 5/145* (2006.01)
*A61B 5/11* (2006.01)
*A61B 8/06* (2006.01)

(52) U.S. Cl.
CPC .......... *A61B 5/026* (2013.01); *A61B 5/02055* (2013.01); *A61B 5/245* (2021.01); *A61B 5/318* (2021.01); *A61B 5/389* (2021.01); *A61B 5/4884* (2013.01); *A61B 5/7275* (2013.01); *A61B 6/501* (2013.01); *A61B 8/00* (2013.01); *A61B 5/01* (2013.01); *A61B 5/021* (2013.01); *A61B 5/024* (2013.01); *A61B 5/055* (2013.01); *A61B 5/0533* (2013.01); *A61B 5/08* (2013.01); *A61B 5/11* (2013.01); *A61B 5/14539* (2013.01); *A61B 6/032* (2013.01); *A61B 6/037* (2013.01); *A61B 8/06* (2013.01); *A61B 2562/0219* (2013.01)

(56) References Cited

U.S. PATENT DOCUMENTS

| | | |
|---|---|---|
| 5,305,746 A | 4/1994 | Fendrock |
| 5,458,117 A | 10/1995 | Chamoun et al. |
| 6,032,064 A | 2/2000 | Devlin et al. |
| 6,728,564 B2 | 4/2004 | Laehteenmaeki |
| 7,054,453 B2 | 5/2006 | Causevic et al. |
| 7,054,454 B2 | 5/2006 | Causevic et al. |
| 7,072,705 B2 | 7/2006 | Miga et al. |
| 7,367,949 B2 | 5/2008 | Korhonen et al. |
| 7,398,115 B2 | 7/2008 | Lynn |
| 7,407,485 B2 | 8/2008 | Huiku |
| 7,447,541 B2 | 11/2008 | Huiku et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |

| | | | |
|---|---|---|---|
| 2003/0093004 A1 | 5/2003 | Sosa et al. | |
| 2004/0163648 A1 | 8/2004 | Burton | |
| 2004/0220644 A1* | 11/2004 | Shalev | A61N 1/0546 607/45 |
| 2004/0243017 A1 | 12/2004 | Causevic | |
| 2005/0113704 A1 | 5/2005 | Lawson et al. | |
| 2006/0217614 A1 | 9/2006 | Takala et al. | |
| 2006/0224421 A1* | 10/2006 | St. Ores | A61B 5/0031 705/4 |
| 2007/0010723 A1 | 1/2007 | Uutela et al. | |
| 2007/0021687 A1* | 1/2007 | Keith | A61B 5/224 600/587 |
| 2007/0167694 A1 | 7/2007 | Causevic et al. | |
| 2007/0249954 A1 | 10/2007 | Virag et al. | |
| 2008/0081980 A1* | 4/2008 | Maschke | A61B 5/0205 600/407 |
| 2008/0139908 A1 | 6/2008 | Kurth | |
| 2008/0167540 A1 | 7/2008 | Korhonen et al. | |
| 2008/0208073 A1 | 8/2008 | Causevic | |
| 2008/0243021 A1 | 10/2008 | Causevic et al. | |
| 2008/0294019 A1 | 11/2008 | Tran | |
| 2009/0290772 A1 | 11/2009 | Avinash et al. | |
| 2011/0053859 A1 | 3/2011 | Deadwyler et al. | |
| 2011/0066055 A1 | 3/2011 | Bharmi et al. | |
| 2011/0245633 A1* | 10/2011 | Goldberg | A61B 5/681 600/301 |
| 2011/0245707 A1 | 10/2011 | Castle et al. | |
| 2013/0030461 A1 | 1/2013 | Marks et al. | |
| 2013/0281788 A1 | 10/2013 | Garrison | |
| 2013/0303900 A1* | 11/2013 | Nowinski | A61B 6/501 600/425 |
| 2014/0187973 A1 | 7/2014 | Brown et al. | |
| 2014/0276074 A1 | 9/2014 | Warner | |
| 2014/0343595 A1 | 11/2014 | Monstadt et al. | |
| 2015/0359547 A1 | 12/2015 | Vale et al. | |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0296690 A1 | 10/2016 | Kume et al. | |
| 2016/0302808 A1 | 10/2016 | Loganathan et al. | |
| 2016/0331255 A1* | 11/2016 | Cheatham, III | G16H 50/30 |
| 2016/0375180 A1 | 12/2016 | Anzai | |
| 2017/0007167 A1 | 1/2017 | Kostic et al. | |
| 2017/0020454 A1* | 1/2017 | Keteyian | A61B 5/6803 |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0140203 A1* | 5/2018 | Wang | A61B 5/0205 |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0153477 A1* | 6/2018 | Nagale | A61B 5/4064 |
| 2018/0185614 A1 | 7/2018 | Garrison et al. | |

FOREIGN PATENT DOCUMENTS

| | | |
|---|---|---|
| JP | 2018118132 A | 8/2018 |
| KR | 20180102877 A | 9/2018 |
| WO | 2013165474 A1 | 11/2013 |
| WO | 2015141317 A1 | 9/2015 |
| WO | 2017192999 A1 | 11/2017 |

(56) References Cited

FOREIGN PATENT DOCUMENTS

| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

OTHER PUBLICATIONS

International Preliminary Report on Patentability from International Application No. PCT/US2018/036228, dated Dec. 19, 2019, 10 pp.
Communication Pursuant to Rules 161(1) and 162 EPC dated Jan. 29, 2020 from counterpart European Application No. 18813006.6, 3 pp.
Response to Communication pursuant to Rules 161(2) and 162 EPC dated Jan. 29, 2020, from counterpart European Application No. 18813006.6, filed Jul. 28, 2020, 13 pp.

* cited by examiner

SYSTEMS AND METHODS FOR DETECTING STROKES

CROSS-REFERENCE TO RELATED APPLICATIONS

The present application claims the benefit of priority of U.S. Patent Application No. 62/516,596, filed Jun. 7, 2017, which is hereby incorporated by reference in its entirety.

FIELD

The present technology is directed to medical devices and, more particularly, to systems and methods for detecting strokes.

BACKGROUND

Stroke is a serious medical condition that can cause permanent neurological damage, complications, and death. Stroke may be characterized as the rapidly developing loss of brain functions due to a disturbance in the blood vessels supplying blood to the brain. The loss of brain functions can be a result of ischemia (lack of blood supply) caused by thrombosis or embolism. During a stroke, the blood supply to an area of a brain may be decreased, which can lead to dysfunction of the brain tissue in that area.

A variety of approaches exist for treating patients undergoing a stroke. For example, a clinician may administer anticoagulants, such as warfarin, or may undertake intravascular interventions such as thrombectomy procedures. However, such treatments may be frequently underutilized due to the failure to timely identify whether a patient is undergoing or has recently undergone a stroke. This is a particular risk with more minor strokes that leave patients relatively functional upon cursory evaluation.

SUMMARY

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., Clause 1 or Clause 16. The other clauses can be presented in a similar manner.

1. A system for detecting strokes, the system comprising:
   a sensor device configured to obtain physiological data from a patient; and
   a computing device communicatively coupled to the sensor device, the computing device configured to:
   receive the physiological data from the sensor device;
   compare the physiological data with reference data; and
   based on the comparison, provide a patient stroke indicator.

2. The system of Clause 1, wherein the sensor device comprises at least one of: an EEG array, an MEG array, an fMRI device, a PET scanner, or a CT scanner.

3. The system of Clause 1, further comprising one or more additional sensor devices configured to obtain additional physiological data from the patient, the one or more additional sensors including at least one of: an accelerometer, a near-infrared sensor, an ultrasound sensor, a heart rate monitor, a blood pressure monitor, a respiration monitor, an electromyography (EMG) sensor, an electrocardiography (ECG) sensor, a galvanic skin sensor, a thermometer, or a camera.

4. The system of Clause 3, wherein the computing device is further configured to:
   receive the additional physiological data from the one or more additional sensor devices;
   compare the additional physiological data with the reference data; and
   based on the comparison, provide a patient stroke indicator.

5. The system of Clause 1, wherein the physiological data comprises brain activity data from a first brain hemisphere of the patient, and wherein the reference data comprises brain activity data from a second brain hemisphere of the patient.

6. The system of Clause 1, wherein the reference data comprises non-patient physiological data.

7. The system of Clause 6, wherein the non-patient physiological data comprises a library of physiological data from stroke patients.

8. The system of Clause 6, wherein the non-patient physiological data comprises a library of physiological data from non-stroke patients.

9. A computer-readable medium storing instructions that, when executed by one or more processors of a computing device, cause the computing device to perform operations, the operations comprising:
   receiving physiological patient data from a sensor device;
   comparing the physiological patient data with reference data; and
   based on the comparison, providing a patient stroke indicator.

10. The computer-readable medium of Clause 9, wherein the sensor device comprises at least one of: an EEG array, an MEG array, an fMRI device, a PET scanner, or a CT scanner, and wherein the physiological patient data comprises brain activity data.

11. The computer-readable medium of Clause 9, wherein the physiological patient data comprises at least one of: motion data, blood constituent data, blood flow data, heart rate data, blood pressure data, respiration data, EMG data, ECG data, pH data, temperature data, or skin galvanic response data.

12. The computer-readable medium of Clause 9, wherein the physiological data comprises brain activity data from a first brain hemisphere of the patient, and wherein the reference data comprises brain activity data from a second brain hemisphere of the patient.

13. The computer-readable medium of Clause 9, wherein the reference data comprises non-patient physiological data.

14. The computer-readable medium of Clause 13, wherein the non-patient physiological data comprises a library of physiological data from stroke patients.

15. The computer-readable medium of Clause 13, wherein the non-patient physiological data comprises a library of physiological data from non-stroke patients.

16. A method for detecting strokes, comprising:
   obtaining physiological data from a patient with a sensor device;
   comparing the physiological data with reference data; and
   based on the comparison, providing a patient stroke indicator.

17. The method of Clause 16, wherein obtaining physiological data from the patient comprises obtaining brain activity data with at least one of: an EEG array, an MEG array, an fMRI device, a PET scanner, or a CT scanner.

18. The method of Clause 16, further comprising obtaining additional physiological data from the patient with one or more additional sensor devices, including at least one of: an accelerometer, a near-infrared sensor, an ultrasound sensor, a heart rate monitor, a blood pressure monitor, a respiration monitor, an electromyography (EMG) sensor, an electrocardiography (ECG) sensor, a galvanic skin sensor, a thermometer, or a camera.

19. The method of Clause 18, further comprising:
comparing the additional physiological data with the reference data; and
based on the comparison, providing a patient stroke indicator.

20. The method of Clause 16, wherein the physiological data comprises brain activity data from a first brain hemisphere of the patient, and wherein the reference data comprises brain activity data from a second brain hemisphere of the patient.

21. The method of Clause 16, wherein the reference data comprises non-patient physiological data.

22. The method of Clause 21, wherein the non-patient physiological data comprises a library of physiological data from stroke patients.

23. The method of Clause 21, wherein the non-patient physiological data comprises a library of physiological data from non-stroke patients.

24. The method of Clause 16, wherein obtaining physiological data from the patient comprises obtaining physiological data while the patient remains passive.

25. The method of Clause 16, wherein obtaining physiological data from the patient comprises:
providing a prompt for the patient to perform one or more actions; and
recording patient physiological data while the patient attempts to perform the one or more actions.

26. The method of Clause 25, wherein the one or more actions comprises at least one of: lifting a limb, moving a hand or fingers, speaking, or smiling.

27. A method for detecting strokes, comprising:
receiving physiological patient data;
comparing the physiological patient data with reference data; and
based on the comparison, providing a patient stroke indicator.

28. The method of Clause 27, wherein the physiological patient data comprises brain activity data.

29. The method of Clause 28, wherein the physiological patient data further comprises at least one of: motion data, blood constituent data, blood flow data, heart rate data, blood pressure data, respiration data, EMG data, ECG data, pH data, temperature data, or skin galvanic response data.

30. The method of Clause 27, wherein the physiological patient data comprises brain activity data from a first brain hemisphere of the patient, and wherein the reference data comprises brain activity data from a second brain hemisphere of the patient.

31. The method of Clause 27, wherein the reference data comprises non-patient physiological data.

32. The method of Clause 31, wherein the non-patient physiological data comprises a library of physiological data from stroke patients.

33. The method of Clause 31, wherein the non-patient physiological data comprises a library of physiological data from non-stroke patients.

Additional features and advantages of the present technology will be set forth in the description below, and in part will be apparent from the description, or may be learned by practice of the subject technology. The advantages of the present technology will be realized and attained by the structure particularly pointed out in the written description and claims hereof as well as the appended drawings.

It is to be understood that both the foregoing general description and the following detailed description are exemplary and explanatory and are intended to provide further explanation of the present technology as claimed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
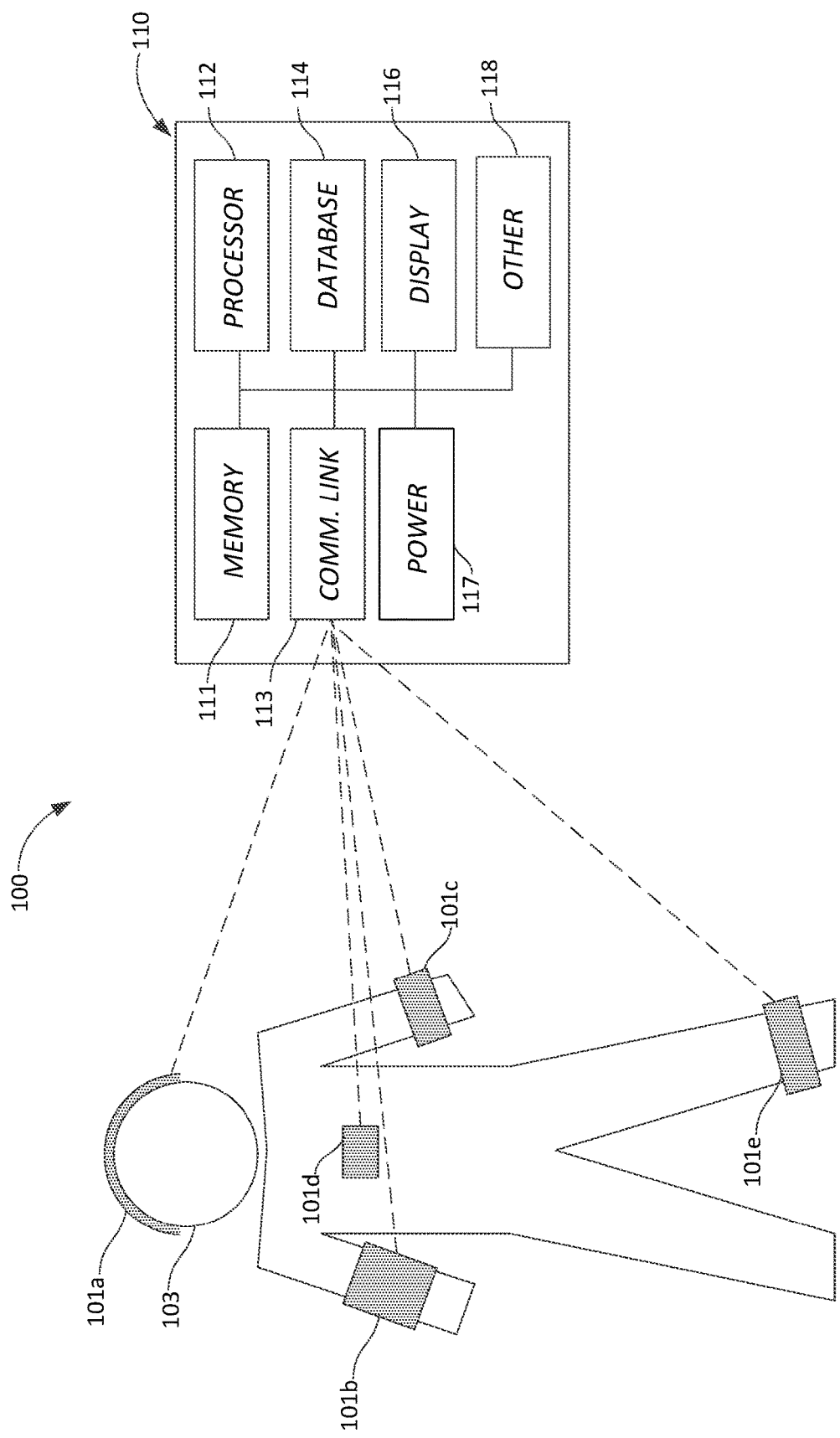
FIG. 1 is a schematic diagram of a stroke detection system configured in accordance with embodiments of the present technology.

It can be difficult to determine whether a patient is suffering from a stroke. Current diagnostic techniques typically involve evaluating a patient for visible symptoms, such as paralysis or numbness of the face, arm, or leg, as well as difficultly walking, speaking, or understanding. However, these techniques may result in undiagnosed strokes, particularly more minor strokes that leave patients relatively functional upon cursory evaluation. Even for relatively minor strokes, it is important to treat the patient as soon as possible because treatment outcomes for stroke patients are highly time-dependent. Accordingly, there is a need for improved methods for detecting strokes.

Embodiments of the present technology enable detection of strokes by obtaining patient sensor data and analyzing the sensor data under passive and/or active conditions, as described in more detail below. For example, an electroencephalogram (EEG) array can be used to sense and record a patient's brain electrical activity. The sensed EEG data set is compared to a reference EEG data set to determine whether a stroke is present. The reference data set can be compiled from EEG measurements of known stroke patients, or from measurements taken from the patient (e.g. from the brain hemisphere opposite that being interrogated). The detection algorithm(s) can be passive (involving measurement of a purely resting patient) or active (involving prompting a patient to perform potentially impaired functionality, such as moving particular muscle groups (e.g., raising an arm, moving a finger, moving facial muscles, etc.) and/or speaking while recording the EEG response). Multiple algorithms of one or both types can be executed and their results combined or considered in the aggregate to determine whether a stroke is present. In various embodiments, sensing modes other than EEG can be used (e.g. magnetoencephalography (MEG), functional magnetic resonance imaging (fMRI), positron emission tomography (PET), computed tomography (CT), accelerometer, near infrared, ultrasound, heart rate, blood pressure, respiration, EMG, ECG, galvanic skin response, temperature, visual). Multiple sensing modes can be used in combination and their respective data can be employed in evaluating the presence of a stroke. The stroke-detection systems disclosed herein can be relatively compact and configured for use in stationary or mobile environments, for example in a hospital emergency room or in an ambulance.

Suitable Systems

The following discussion provides a brief, general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a schematic diagram of system 100 configured in accordance with an embodiment of the disclosed technology. The system 100 includes a variety of sensor devices 101a-d (collectively "sensor devices 101") disposed over different regions of interest of a patient 103. For example, the sensor devices 101 can include an EEG sensor array 101a disposed over a patient's head, a blood pressure monitor 101b disposed over a patient's arm or other suitable location to monitor and record a patient's blood pressure, a pulse oximeter 101c disposed over a patient's finger or another location to monitor a patient's pulse, an EKG sensor 101d or other heart-recording device configured to monitor a patient's cardiac activity, and/or an accelerometer 101e disposed on a patient's ankle or other suitable location to monitor patient movement. These particular sensor devices 101 are exemplary, and in various embodiments the sensors employed can vary. For example, the EEG sensor array 101a can be replaced with an MEG array, an fMRI machine, a CT scanner, or other suitable device configured to monitor and record a patient's brain activity. Additionally, more or fewer of the particular sensors identified here may be used in any particular instance, for example the system may include only the EEG sensor array 101a in some embodiments. In other embodiments, additional sensors can be employed, for example cameras for visual monitoring of a patient, a skin galvanometer for monitoring the conductivity of the patient's skin, accelerometers, thermometers, hygrometers, blood pressure sensors, altimeters, gyroscopes, magnetometers, proximity sensors, barometers, hall effect sensors, and any other suitable sensor for monitoring physiological characteristics of the patient 103.

One or more of the sensor devices 101 can be communicatively coupled to a processing subsystem 110. The processing subsystem 110 can, in some embodiments, be similar to the digital signal converter 28 and/or the EEG monitor 12 described below with respect to FIGS. 2-4. The processing subsystem 110 comprises several components including memory 111 (e.g., one or more computer readable storage modules, components, devices) and one or more processors 112. The memory 111 can be configured to store information (e.g., signal data, subject information or profiles, environmental data, data collected from one or more sensors, media files) and/or executable instructions that can be executed by the one or more processors 112. The memory 111 can include, for example, instructions for analyzing patient data to determine whether a patient is undergoing or has recently undergone a stroke.

The processing subsystem 110 also includes communication components 113 (e.g., a wired communication link and/or a wireless communication link (e.g., Bluetooth, Wi-Fi, infrared and/or another wireless radio transmission network)) and a database 114 configured to store data (e.g., signal data acquired from the sensor devices 101, reference data, equations, filters) used in the stroke detection techniques disclosed herein. One or more displays 116 can provide video output and/or graphical representations of data obtained by the system 100. A power supply 117 (e.g., a power cable connected to a building power system, one or more batteries and/or capacitors) can provide electrical power to components of the processing subsystem 110 and/or the system 100. In embodiments that include one or more batteries, the power supply 117 can be configured to recharge, for example, via a power cable, inductive charging, and/or another suitable recharging method. Furthermore, in some embodiments, the processing subsystem 110 may one or more additional components 118 (e.g., one or more microphones, cameras, Global Positioning System (GPS) sensors, Near Field Communication (NFC) sensors).

In some embodiments, the processing subsystem 110 may include one or more components partially or wholly incorporated into one or more of the sensor devices 101. In other embodiments, however, the processing subsystem 110 may include components remote from the sensor devices 101 and connected thereto by a communication network (e.g., the Internet and/or another network). In some embodiments, for example, at least a portion of the processing subsystem 110 may reside on a mobile device (e.g., a mobile phone, a tablet, a personal digital assistant) and/or a computer (e.g., a desktop computer, a laptop) communicatively coupled to the sensor devices 101.

Figure 2:
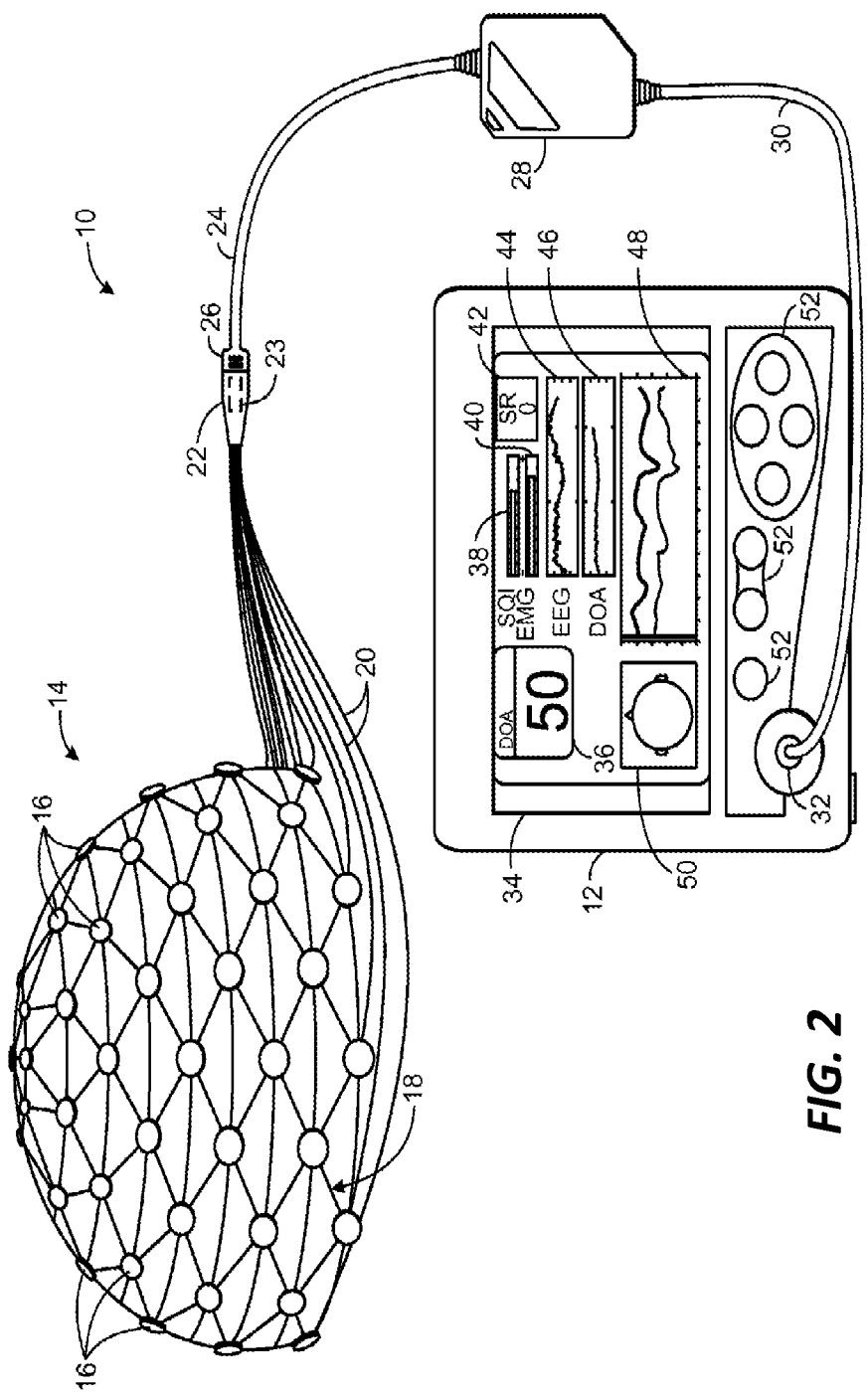
FIG. 2 is a schematic diagram of a patient monitoring system including an EEG monitor and an EEG sensor array, in accordance with embodiments of the present technology.

FIG. 2 illustrates an embodiment of a patient monitoring system 10 including an electroencephalography (EEG) monitor 12 that may be used in conjunction with an EEG sensor array 14. The EEG sensor array 14 includes a plurality of electrodes 16 that are used to acquire one or more EEG signals from a patient, which may be used by the monitor 12 to determine one of more physiological characteristics of the patient. For example, the monitor 12 may be configured to determine the presence or absence of a stroke or other neurological condition based on the one or more EEG signals from the plurality of electrodes 16.

With continued reference to FIG. 2, the electrodes 16 may be formed from any suitable conductive material or materials to enable the electrodes to perform electrical measurements on the patient. In some embodiments, the electrodes 16 may be formed from flexible conductive materials, such as one or more conductive inks, to provide enhanced flexibility and conformance to patient tissue. It should be understood that the EEG sensor array 14 may include additional components and/or materials, such as one or more structural layers, foam layers, adhesive layers, sponges, conductive gels, etc. Additionally, in some embodiments, the EEG sensor array 14 may be configured for a one-time use and may be discarded after use by one patient. In other embodiments, the EEG sensor array 14 may be reusable or at least partially reusable. In yet other embodiments, the EEG sensor array can be substituted for another type of sensing device, for example an MEG array, an fMRI, CT scanner, accelerometer, near infrared, ultrasound, heart rate, blood pressure, respiration, EMG, ECG, skin galvanometer, thermometer, etc.

The electrodes 16 may be supported by a framework 18, which may be configured to facilitate proper placement of the electrodes 16 on a patient's head. The framework 18 may flexible (e.g., elastic), semi-rigid, or rigid, and may be formed of any suitable materials. In certain embodiments, the framework 18 may enable the electrodes 16 to be placed on the patient's head without scalp preparation (e.g., shaving) or abrasion. In one embodiment, the framework 18 may be a Geodesic Sensor Net. Further, in some embodiments, different sized frameworks 18 may be constructed to accommodate different sized patients (e.g., neonatal, pediatric, or adult). In other embodiments, the framework 18 may be one-size fits all or may include adjustment features to adjust the framework 18 to fit about the patient's head. Additionally, the framework 18 may include indicia to facilitate the proper placement of the framework 18 and electrodes 16 about the patient's head. For example, the indicia can include text, numbers, graphics, symbols, and/or changes in color that may provide information to a caregiver regarding the proper placement of the framework 18 and electrodes 16 about the patient's head.

It may be desirable to utilize an EEG sensor array 14 to increase the specificity and the resolution (e.g. spatial and/or temporal) of the measurements. Accordingly, in some embodiments, the EEG sensor array 14 may include 6-500 of the electrodes. In certain embodiments, the EEG sensor array 14 may include 64-256 or the electrodes 16. Each electrode 16 may be coupled to a respective lead 20 (e.g., a conductor, channel, etc.), which may be configured to transmit signals to and/or from a respective electrode 16. It should be noted that the illustrated embodiment does not show a lead 20 coupled to each electrode 16, and a few representative leads 20 have been illustrated. In certain embodiments, the EEG sensor array 14 may include a connector 22, such as a paddle connector, which may be configured to receive the plurality of leads 20. In certain embodiments, the connector 22 may include a memory device 23, which may be configured to store information about the EEG sensor array 14, such as the number of electrodes 16 of the EEG sensor array 14, the type or model of the EEG sensor array 14, calibration data related to the electrodes 16 (e.g., a range of acceptable impedance values), which may be provided to the monitor 12. It should be appreciated that the location of the memory device 23 is not limited to the connector 22, and the memory device 23 may be disposed in alternate locations in other embodiments.

The connector 22 may be coupled to a cable 24 (e.g., a patient interface cable) via a connector 26. The cable 24 may be coupled to a digital signal converter 28. As will be described in more detail below, the digital signal converter 28 receives, filters, and processes the EEG signals for each channel (e.g., each lead 20). The digital signal converter 28 is coupled to a cable 30, which may be coupled to the monitor 12 via a port 32. In certain embodiments, the digital signal converter 28 may be embedded in the monitor 12. However, it may be desirable to provide the digital signal converter 28 external to the monitor 12 such that the digital signal converter 28 may be closer to the patient's head where the EEG signals may be subject to less interference from other medical equipment.

The monitor 12 may be configured to calculate physiological characteristics relating to one or more EEG signals received from the EEG sensor array 14. For example, the monitor 12 may be configured to algorithmically determine the presence or absence of a stroke or other neurological condition from the EEG signal. In certain embodiments, the presence of a stroke or other condition may be determined using spontaneous EEG signals. That is, in certain embodiments, the presence of a stroke, etc. may not be determined using evoked potentials (e.g., in response to a stimulus). In certain embodiments, the monitor 12 may make a stroke determination for each electrode 16 (e.g., channel) or may make a stroke determination using EEG signals acquired from two or more selected electrodes (e.g., from a region of interest). In one embodiment, the monitor 12 may make a stroke determination based on measurements or determinations from one or more regions of the patient's head. Additionally, as will be described in more detail below, the monitor 12 may be configured to monitor the EEG signals and/or make a stroke determination for particular regions of interest, such as the quadrants of the patient's head.

The monitor 12 may also include a display 34 configured to display physiological characteristics, historical trends of physiological characteristics, other information about the system, and/or alarm indications. For example, the monitor 12 may display one or more indices 36 (e.g., a stroke indicator, a depth of anesthesia index, etc.) of the patient, such as a depth of anesthesia (DOA) value 36. In some embodiments, as will be described in more detail below, the display 34 may display an anesthesia index (e.g., the DOA value 36) for each desired region of the patient's head. The DOA value 36 may represent a dimensionless number (e.g., ranging from 0, i.e., silence, to 100, i.e., fully awake and alert) output from a multivariate discriminant analysis that quantifies the overall bispectral properties (e.g., frequency, power, and phase) of the EEG signal. For example, a DOA value 36 between 40 and 60 may indicate an appropriate level for general anesthesia.

The monitor 12 may also display a signal quality index (SQI) bar graph 38 (e.g., ranging from 0 to 100) which measures the signal quality of the EEG channel source(s) (e.g., the electrode(s) 16 used to acquire the EEG signal) based on impedance data, artifacts, and other variables. In certain embodiments, the monitor 12 may also display an electromyograph (EMG) bar graph 40 (e.g., ranging from 30 to 55 decibels) which indicates the power (e.g., in decibels) in the frequency range of 70 to 110 Hz. The frequency range may include power from muscle activity and other high-frequency artifacts. The monitor 12 may further display a suppression ratio (SR) 42 (e.g., ranging from 0 to 100 percent), which represents the percentage of epochs over a given time period (e.g., the past 63 seconds) in which the EEG signal is considered suppressed (i.e., low activity). In certain embodiments, the monitor 12 may also display a burst count for the number of EEG bursts per minute, where a "burst" is defined as a short period of EEG activity preceded and followed by periods of inactivity or suppression.

Additionally, the monitor 12 may display one or more EEG waveforms 44. For example, the monitor 12 may receive one or more EEG signals from one or more electrodes 16 and may display the EEG waveforms 44 for each received EEG signal. In certain embodiments, the EEG waveform 42 may be filtered. Additionally the monitor 12 may display one or more depth of anesthesia waveforms 46. The monitor 12 may also display trends 48 over a certain time period (e.g., one hour) for EEG, DOA, SR, EMG, SQI, and/or other parameters. In certain embodiments, the monitor 12 may display stepwise instructions for placing the EEG sensor array 14 on the patient and/or an image illustrating the proper placement of the EEG sensor array 14 on a patient's head. Further, as will be described in more detail below, the monitor 12 may display one or more topographical color maps 50 of the EEG activity of the patient's head.

Additionally, the monitor 12 may include various control inputs 52 (e.g., buttons and switches) to facilitate management and operation of the monitor 12. For example, the monitor 12 may include function keys, a power switch, adjustment buttons, an alarm silence button, and so forth. The control inputs 52 may enable a user to select or input a specific sensor type or model, such as the specific number of electrodes 16 of the EEG sensor array 14. This may enable the monitor 12 to select the appropriate instructions for analyzing the EEG signals and making stroke determinations based on the particular EEG sensor array 14. Further, in some embodiments, the control inputs 52 may enable a user to select electrode(s) 16 of interest to monitor the EEG signals and/or make stroke determinations from selected electrode(s) or groups of electrodes.

Figure 3:
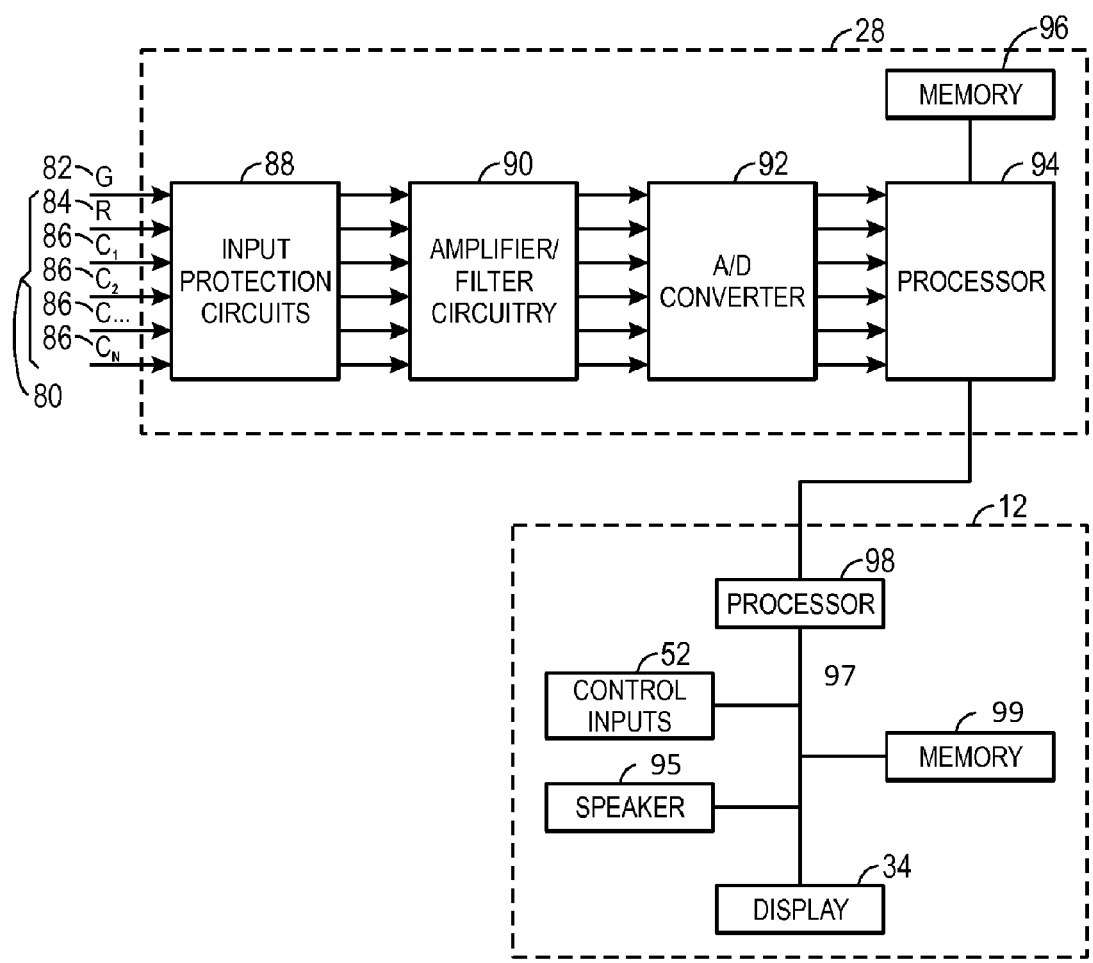
FIG. 3 is a block diagram of the patient monitoring system of FIG. 2, in accordance with embodiments of the present technology.

One embodiment of the various components of the digital signal converter 28 and the monitor 12 is illustrated with respect to FIG. 3. While the illustrated embodiment is directed toward a digital signal converter 28 that is external to the monitor 12, it should be appreciated that, in other embodiments, the digital signal converter 28 may be integrated into the monitor 12. As illustrated, the digital signal converter 28 is configured to receive a plurality of EEG signals 80 from the EEG sensor array 14. The digital signal converter 28 is configured to receive at least three EEG signals 80 to determine the presence or absence of a stroke or other neurological condition in the patient. In particular, the digital signal converter 28 may receive a ground signal 82 from a ground electrode of the EEG sensor array 14, a reference signal 84 from a reference electrode of the EEG sensor array 14, and one or more sensing signals 86 from one or more sensing electrodes of the EEG sensing array 14. In certain embodiments, the reference electrode may be positioned about the center of the top of the patient's head. Further, in some embodiments, one or more of the sensing signals 86 may be used to monitor artifacts from muscular movements, such as eye blinking or movement. As will be described in more detail below, the monitor 12 may be configured to select certain electrodes of the EEG sensor array 14 to monitor specific regions of the patient's head. Further, the monitor 12 may be configured to select which electrodes are to be used for monitoring artifacts and which electrodes are to be used for monitoring physiological characteristics of the patient.

In certain embodiments, the digital signal converter 28 and/or the monitor 12 may include one or more input protection circuits 88 to filter the EEG signals 80 and may include amplifier/filter circuitry 90 to remove DC and high frequency components. Additional components of the digital signal converter 28 and/or the monitor 12 may include one or more analog-to-digital (A/D) converters 92, a processor 94, and a memory 96 (e.g., RAM, ROM, flash memory, etc.) coupled to the processor 94, which may be configured to store instructions that may be read and executed by the processor 94 to implement the present techniques. The monitor 12 may be configured to send signals to and/or receive signals from the digital signal converter 28. In some embodiments, the monitor 12 may receive calculated physiological characteristics from the processor 94. In other embodiments, the monitor 12 may receive digitized signals from the one or more A/D converters 92 or filtered digitized signals from the processor 94. The monitor 12 may also include one or more memory devices 99 (e.g., a RAM and/or a ROM) coupled to the processor 98 by an internal bus 97. The one or more memory devices 99 may be configured to store instructions that may be read and executed by the processor 98 to implement the present techniques. In certain embodiments, the monitor 12 may store instructions that are specific to a particular sensor type or model. For example, the monitor 12 may store a plurality of instructions for analyzing EEG signals and determining the presence or absence of a stroke or other neurological condition and may select a particular set of instructions from the memory 99 based on the number of electrodes 16 of the EEG sensor array 14. The monitor 12 may also include the display 34, the control inputs 52, and a speaker 95 coupled to the internal bus 97.

As noted above, the monitor 12 may be configured to dynamically select which electrodes 16 of the EEG sensor array 14 to use for the stroke determination. The memory 99 of the monitor 12 may store one or more default settings for the electrodes 16 to be used, which may be determined and selected based on at least in part upon the type of EEG sensor array 14 (e.g., the number of electrodes 16 in the EEG sensor array 14), information relating to the patient, surgical procedure, and/or anesthetics used with the patient, and/or input provided by the caregiver. The monitor 12 may be configured to adjust the selected default setting or select a new default setting (i.e., to select one or more different electrodes 16 or only a subset of the available electrodes 16) in response to a determination that the EEG signal may contain artifacts. For example, one or more of the sensing signals 86 may be used by the monitor 12 to monitor artifacts, and the monitor 12 may determine that artifacts are present in a sensing signal 86. Accordingly, the monitor 12 may be configured to select a different electrode 16 to use to monitor the patient's EEG and to make the stroke determination. It should be appreciated that the monitor 12 may dynamically cycle between the electrodes 16 of the EEG sensor array 14 until a desired signal quality is reached. In one embodiment, in an implementation in which specific regions of the head are being monitored and compared to one another, the monitor 12 may provide instructions to cycle through the electrodes 16 in one or more quadrants to find either satisfactory or the best signal quality within an individual quadrant.

In some embodiments, a user may be configured to input the desired electrodes 16 (e.g., for a region of interest) using one or more of the control inputs 52. For example, the electrodes 16 of the EEG sensor array 14 may be labeled (e.g., numerically, alphabetically, or a combination thereof) and the user may be configured to input the corresponding label for the desired electrodes 16 via the control inputs 52. To facilitate the selection, the display 40 may be configured to display a graphical representation of the EEG sensor array 14. In certain embodiments, the monitor 12 may be configured to download information from the memory device 23 of the EEG sensor array 14 to provide the monitor 12 with information regarding the type of EEG sensor array 14, such as the number of electrodes 16. This information may be used by the monitor 12 to create a graphical representation of the specific EEG sensory array 14 or to select a graphical representation of the specific EEG sensor array 14 from a set of graphical representations for various EEG sensor arrays 14.

Figure 4:
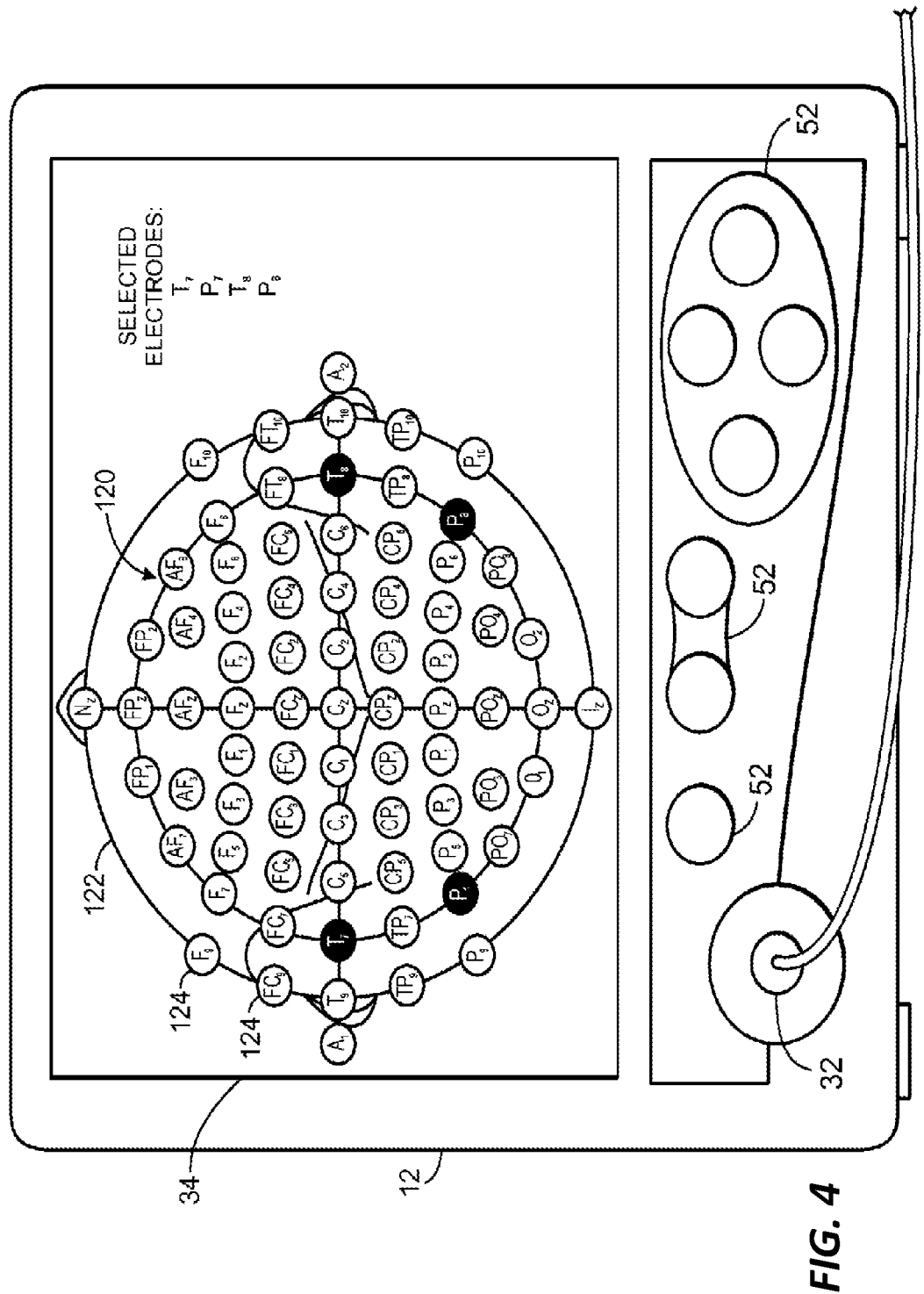
FIG. 4 is a schematic diagram of a display of the EEG monitor of FIG. 2 illustrating a graphical illustration of the EEG sensor array of FIG. 2, in accordance with embodiments of the present technology.

As illustrated in FIG. 4, the display 34 may display a graphical representation 120 of the EEG sensor array 14 and graphical representation 122 of a patient's head. Providing the graphical representation 122 of the patient's head may be desirable to facilitate a caregiver in quickly selecting the desired electrodes 16 based upon one or more regions of interest of the patient's head. In certain embodiments, the display 34 may also be configured to display labels 124 (e.g., numerical, alphabetical, or a combination thereof) for each electrode 16 or for selected electrodes 16. It should be appreciated that the labels 124 may be provided in any suitable form. For example, in one embodiment, the labels 124 may be disposed proximate to the respective electrode 16.

Suitable Methods

Figure 5:
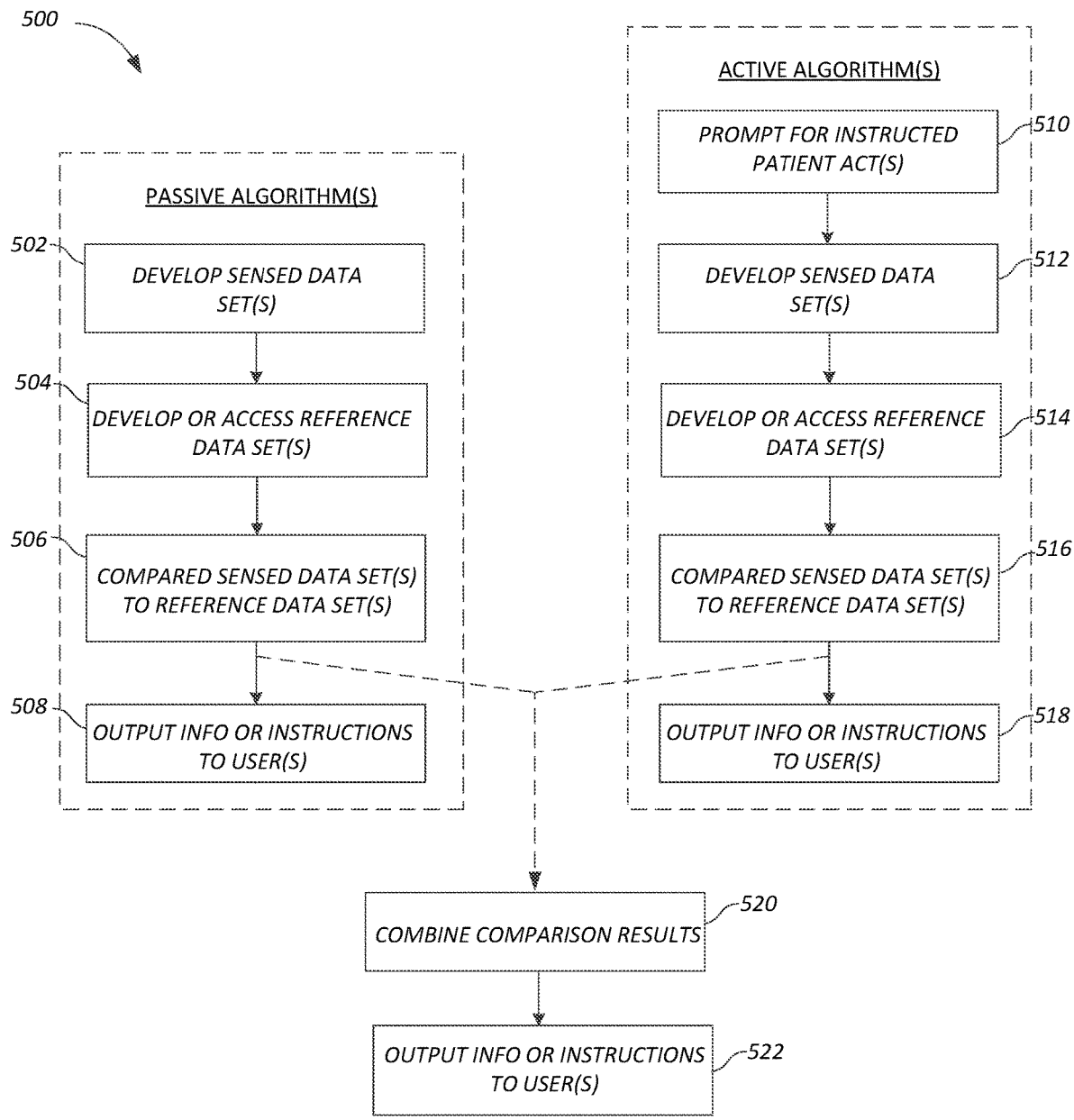
FIG. 5 is a schematic diagram of the process flow for detecting strokes in a patient in accordance with embodiments of the present technology.

FIG. 5 is a flow diagram of a process 500 configured in accordance with an embodiment of the present technology. The process 500 can include instructions stored, for example, in the memory (e.g., memory 111 of FIG. 1 or memory 99 of FIG. 3) that are executable by the one or more processors (e.g., processor 112 of FIG. 1 or processor 98 of FIG. 3). In some embodiments, portions of the process 500 are performed by one or more hardware components (e.g., the sensor devices 101 of FIG. 1, the digital signal converter 28 of FIG. 3, or the EEG array 14 of FIG. 2). In certain embodiments, portions of the process 500 are performed by a device external to the system 100 of FIG. 1 or the system 10 of FIG. 2.

As illustrated, the process 500 can include both a passive component and an active component, which can optionally be combined. In some embodiments, the process 500 includes only the passive component or only the active component, while in other embodiments of the process 500 both the active and passive components can be employed and combined for improved stroke detection. The active and passive components can be performed sequentially in either order (i.e., passive first, then active, or vice versa), or in some embodiments at least portions of the passive and active components may be performed in parallel. For example, the comparison of sensed data set(s) to reference data set(s) in block 506 (passive component) and block 516 (active component) may be performed in parallel in at least some embodiments.

The passive component of process 500 begins in block 502 with developing sensed data set(s). For example, the system can receive physiological patient data from one or more sensors (e.g., the sensor devices 101 of FIG. 1 or the EEG array 14 of FIG. 2). The physiological patient data can include brain activity data recorded by the EEG array or other brain sensing device as well as data from one or more additional sensors. The additional sensors can include, for example, one or more accelerometers (for measuring patient movement of head or limb), blood pressure monitors, heart rate monitors, ultrasound probes, infrared sensors, temperature sensors, galvanic sensors, and/or pH sensors. Patient data from one or more of these sensor devices is recorded and stored in the sensed data set(s).

In some embodiments, certain sensor data can be used to remove aberrations from the sensed data set. For example, accelerometer data may indicate gross movement (e.g., a bumpy ambulance ride) and can remove the resulting artifacts from the data. The additional sensor data can be useful in identifying a stroke, for example heart rate monitors can detect arrhythmia (or other heart rate profiles) that can be indicative of stroke. Ultrasound probes can measure blood flow volume or velocity, and infrared sensors can measure blood constituent levels such as oxygenation. Galvanic sensors measuring conductivity of a patient's skin, and pH sensors measuring acidity of a patient's skin can likewise provide useful parameters for stroke detection.

In block 504, the process 500 develops or accesses reference data set(s). Developing reference data sets can include measuring the patient to create reference data, for example by obtaining measurements taken from brain regions other than the particular brain region being interrogated for possible stroke (e.g., the brain hemisphere opposite to the hemisphere being interrogated). Accessing reference data set(s) includes obtaining or querying external reference data stored in the system or remotely. The reference data can be non-patient data (i.e., patient obtained from sources other than the particular patient being evaluated). For example, a library of physiological data obtained from stroke patients and/or normal populations can be obtained to provide reference data for the system. The reference data can include measurements of brain activity as well as one or more additional parameters, such as blood pressure, heart rate, ultrasound measurements, blood oxygenation, temperature, skin galvanic response, pH, or any other suitable physiological data that aids in identifying a patient stroke.

In block 506, the sensed data set(s) are compared to the reference data set(s) to determine whether a stroke is indicated. Comparison of the two data sets can include statistical techniques for measuring closeness or fit, for example machine learning techniques including but not limited to logistic regression, deep learning neural networks, extreme gradient boosting machines, support vector machines, to develop a binary classifier for stroke using reference stroke databases and non-stroke databases. In some embodiments, each type of data (e.g., brain activity data as recorded by an EEG monitor, patient temperature data, blood pressure data, etc.) can be compared separately, while in other embodiments the different types of physiological patient data can be combined for comparison between the sensed data sets and the reference data sets. Based on this comparison, the system can provide a patient stroke indicator. The patient stroke indicator can be, for example, a binary output of stroke/non-stroke condition, a probabilistic indication of stroke likelihood, or other output relating to the patient's condition and likelihood of having suffered a stroke.

In block 508, the process 500 outputs information or instructions to the user(s). The information or instructions can be output via a display device (e.g., the display 116 of FIG. 1 or the display 34 of FIGS. 2-4). For example, if a stroke is identified in block 506, then the system may provide instructions to route the patient to a comprehensive stroke treatment center or otherwise flag the patient for treatment. In embodiments in which the process 500 is performed while the patient is in an ambulance, the process 500 can output information or instructions to an emergency medical technician (EMT) or other personnel in the rear of the ambulance and/or to the ambulance driver. In some embodiments, the display to the ambulance driver can include navigational information such as a map and instructions to take the patient to a particular hospital or facility with a stroke center.

The active component of the process 500 begins in block 510 by providing prompts for instructed patient act(s). The prompts for instructed acts can be provided to a user via a display device (e.g., the display 116 of FIG. 1 or the display 34 of FIGS. 2-4). In some embodiments, the prompts include instructions for the patient to perform particular acts or movements, such as lifting an arm or leg, moving a hand or fingers, speaking, smiling, recognition of body, clapping, etc. In some embodiments, these prompts can be provided in succession, and patient data can be obtained after each prompt while the patient responds (or fails to respond) to the particular instructions. In some embodiments, accelerometer data can be used to monitor patient movement in response to the provided prompts.

In block 512, the process 500 develops sensed data set(s). As described above with respect to block 502 in the passive component, the system can receive physiological patient data from one or more sensors (e.g., the sensor devices 101 of FIG. 1 or the EEG array 14 of FIG. 2) which can include brain activity data in addition to data from one or more additional sensors.

The process continues in block 514 with developing or accessing reference data set(s). Similar to the process described above with respect to block 504 in the passive component, the system can develop a reference data set by obtaining measurements taken from a brain region that is separated from the brain region being interrogated for possible stroke. The process 500 can also access reference data sets by obtaining or querying an external library of physiological data obtained from stroke patients and/or normal populations that is stored in the system or remotely. The reference data sets can include data recorded under similar active conditions to enable fruitful comparison between the sensed data and the reference data.

In block 516, the sensed data set(s) and reference data set(s) are compared. As described in block 506 of the passive component, comparison of the two data sets can include statistical techniques for measuring closeness or fit, for example machine learning techniques (e.g., logistic regression, deep learning neural networks, extreme gradient boosting machines, support vector machines). Based on this comparison, the process 500 provides a patient stroke indicator, for example indicating whether the patient is undergoing or has recently suffered a stroke.

In block 518, the process 500 outputs information or instructions to the user(s), similar to the process described above with respect to block 508 in the passive component. The information or instructions can be output via a display device (e.g., the display 116 of FIG. 1 or the display 34 of FIGS. 2-4). For example, if a stroke is identified in block 516, then the system may provide instructions to route the patient to a comprehensive stroke treatment center or otherwise flag the patient for treatment.

Optionally, the process 500 can include a combined component in which the output from block 506 of the passive component (which includes comparison of the sensed data sets and reference data sets under passive conditions) and the output from block 516 (which includes comparison of the sensed data sets and reference data sets under active conditions) are combined in block 520. These combined results are then evaluated comprehensively, for example by using a weighted score or other algorithm for combining the two outputs to provide a patient stroke indicator, such as indicating whether or not a patient has likely suffered or is currently suffering from a stroke.

Continuing with this optional component, in block 522 information or instructions are output to the user based on the evaluation of the combined comparison in block 520. As indicated above with respect to blocks 508 and 518, the information output can include indication of possible stoke, instructions to deliver the patient to a stroke treatment facility, or any other pertinent information based on the comparison in block 520.

Figure 6A:
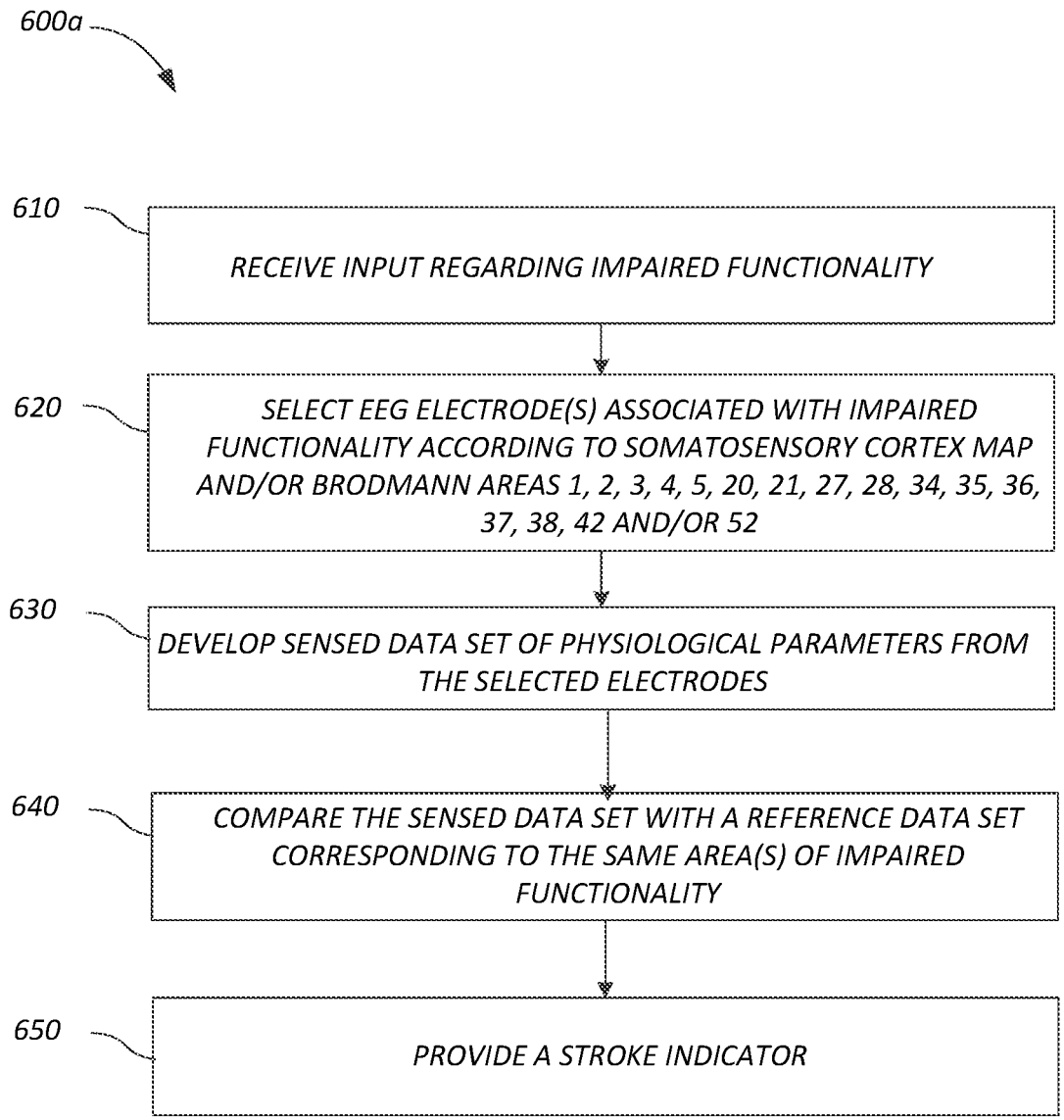
FIG. 6A is a schematic diagram of the process flow for detecting strokes in a patient in accordance with embodiments of the present technology.

FIG. 6A is a schematic diagram of a process flow 600a for detecting strokes in a patient in accordance with embodiments of the present technology. The process 600a can include passive and/or active components as described above with reference to the process 500. The process 600a begins by receiving input regarding impaired functionality experienced by the patient (block 610). For example, if the patient experiences a loss of motor function related to a particular body part (e.g., arm, finger, facial muscles etc.) and/or speech, the impaired functionality associated with the symptom of the stroke is input to a computer (e.g., the processing subsystem 110 of FIG. 1 or the monitor 14 of FIG. 2). The process 600a continues by selecting one or more of the EEG electrodes at locations associated with the impaired functionality according to the somatosensory cortex map of the primary motor cortex and/or one or more of Brodmann Areas 1, 2, 3, 4, 5, 20, 21, 22, 28, 34, 35, 36, 37, 38, 42 and/or 52. The somatosensory cortex integrates sensory information from the body according to a map based on the primary motor cortex located at the post central gyms (block 620).

The process 600a continues by developing a sensed data set from the selected EEG electrodes (block 630), and then comparing the sensed data set from the selected EEG electrodes to reference data set(s) (block 640). The reference data set (block 640) can be a library of physiological data from stroke patients, such as EEG measurements corresponding to the same areas of impaired functionality of the specific patient used to select the EEG electrodes in block 620. In some embodiments, the EEG measurements of the library of physiological data can be associated with the particular areas of the somatosensory cortex map and/or Brodmann Areas that are selected according to the impaired functionality in block 620. Based on the comparison (block 640), the process 600a continues by providing a patient stroke indicator (block 650).

Figure 6B:
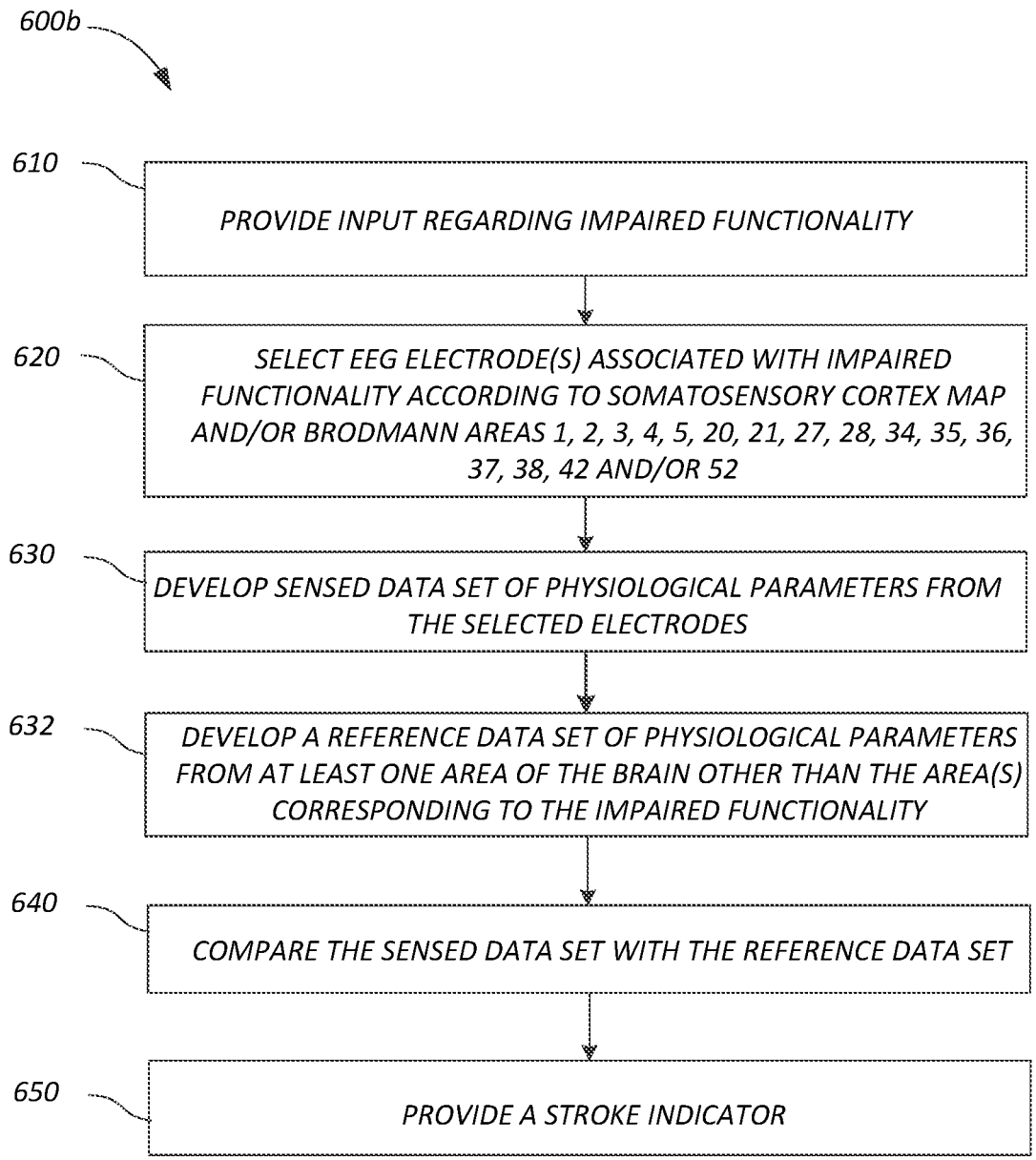
FIG. 6B is a schematic diagram of the process flow for detecting strokes in a patient in accordance with embodiments of the present technology.

FIG. 6B is a schematic diagram of a process flow 600b for detecting strokes in a patient in accordance with embodiments of the present technology. The process 600b is similar to the process 600a described above with reference to FIG. 6A, but instead of comparing the sensed data with a library of physiological data, the sensed data in process 600b is compared to other measurements taken from different areas of the brain of the same patient. The process 600b begins with receiving input regarding the impaired functionality experienced by a patient (block 610), and selecting one or more of the EEG electrodes at locations associated with the impaired functionality according to the somatosensory cortex map of the primary motor cortex and/or one or more of Brodmann Areas 1, 2, 3, 4, 5, 20, 21, 22, 28, 34, 35, 36, 37, 38, 42 and/or 52 (block 620), as described above with reference to FIG. 6A. The process 600b further includes developing a sensed data set of physiological parameters from the selected electrode(s) (block 630).

The process 600b further includes developing a reference data set of physiological parameters from at least one area of the brain of the patient other than the area(s) corresponding to impaired functionality (block 632). For example, if the patient appears to experience impaired functionality of facial muscles, the EEG electrodes can be selected to correspond to a portion of the somatosensory cortex associated with controlling facial muscles in block 620 and the reference data in block 632 can be developed by measuring brain function from one or more of the EEG electrodes along the primary motor cortex associated with different functionality (e.g., movement of arms or fingers). The process 600b continues at block 640 by comparing the sensed data from the selected electrodes in block 620 with the reference data sensed from other areas of the brain in block 632. Based on the comparison (block 640), the process 600b continues by providing a patient stroke indicator (block 650).

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A system for detecting strokes, the system comprising:
  a sensor device configured to obtain physiological data from a patient, the sensor device comprising a sensor array including a plurality of electrodes configured to acquire one or more physiological signals from the patient, the physiological data including at least brain activity data; and
  a computing device communicatively coupled to the sensor device, the computing device configured to:
    receive input regarding an impaired functionality experienced by the patient;
    select one or more of the plurality of electrodes at brain locations of the patient associated with the impaired functionality;
    generate passive physiological analysis results by:
      receiving passive physiological data from the selected one or more of the plurality of electrodes, the passive physiological data comprising physiological data obtained while the patient remains passive; and
      comparing the passive physiological data with passive reference data, the passive reference data received from one or more of the plurality of electrodes at brain locations other than those associated with the impaired functionality;
    generate active physiological analysis results by:
      providing a prompt for the patient to perform one or more actions;
      receiving active physiological data from the selected one or more of the plurality of electrodes, the active physiological data comprising physiological data obtained while the patient attempts to perform the one or more actions; and
      comparing the active physiological data with active reference data, the active reference data received from one or more of the plurality of electrodes at brain locations other than those associated with the impaired functionality; and
    based on the passive physiological analysis results and the active physiological analysis results, provide a patient stroke indicator.

2. The system of claim 1, wherein the sensor device comprises at least one of: an EEG array, an MEG array, an fMRI device, a PET scanner, or a CT scanner.

3. The system of claim 1, further comprising one or more additional sensor devices configured to obtain additional physiological data from the patient, the one or more additional sensors including at least one of: an accelerometer, a near-infrared sensor, an ultrasound sensor, a heart rate monitor, a blood pressure monitor, a respiration monitor, an electromyography (EMG) sensor, an electrocardiography (ECG) sensor, a galvanic skin sensor, a thermometer, or a camera.

4. The system of claim 3, wherein the computing device is further configured to:
receive the additional physiological data from the one or more additional sensor devices;
compare the additional physiological data with additional reference data; and
based on the comparison, provide a patient stroke indicator.

5. The system of claim 1, wherein the passive physiological data comprises brain activity data from a first brain hemisphere of the patient, and wherein the passive reference data comprises brain activity data from a second brain hemisphere of the patient.

6. The system of claim 1, wherein the passive reference data further comprises non-patient physiological data.

7. The system of claim 1, the passive reference data comprising a library of physiological data obtained from a plurality of stroke patients, the library of physiological data comprising measurements from each of the plurality of patients corresponding to brain locations associated with the impaired functionality.

8. The system of claim 1, the passive reference data comprising physiological data taken from at least one location of the brain of the patient other than the brain locations of the patient corresponding to the impaired functionality.

9. A computer-readable medium storing instructions that, when executed by one or more processors of a computing device, cause the computing device to perform operations, the operations comprising:
receiving input regarding an impaired functionality experienced by the patient;
selecting one or more of a plurality of electrodes in a sensor array at brain locations of the patient associated with the impaired functionality;
generating passive physiological analysis results by:
receiving passive physiological data from the selected one or more of the plurality of electrodes, the passive physiological data comprising physiological data obtained while the patient remains passive; and
comparing the passive physiological data with passive reference data, the passive reference data received from one or more of the plurality of electrodes at brain locations other than those associated with the impaired functionality;
generating active physiological analysis results by:
providing a prompt for the patient to perform one or more actions;
receiving active physiological data from the selected one or more of the plurality of electrodes, the active physiological data comprising physiological data obtained while the patient attempts to perform the one or more actions; and
comparing the active physiological data with active reference data, the active reference data received from one or more of the plurality of electrodes at brain locations other than those associated with the impaired functionality; and
based on the passive physiological analysis results and the active physiological analysis results, providing a patient stroke indicator.

10. The computer-readable medium of claim 9, wherein the sensor device comprises at least one of: an EEG array, an MEG array, an fMRI device, a PET scanner, or a CT scanner, and wherein the physiological patient data comprises brain activity data.

11. The computer-readable medium of claim 9, wherein the passive physiological patient data comprises at least one of: motion data, blood constituent data, blood flow data, heart rate data, blood pressure data, respiration data, EMG data, ECG data, pH data, temperature data, or skin galvanic response data.

12. The computer-readable medium of claim 9, wherein the passive physiological data comprises brain activity data from a first brain hemisphere of the patient, and wherein the passive reference data comprises brain activity data from a second brain hemisphere of the patient.

13. The computer-readable medium of claim 9, wherein the passive reference data further comprises non-patient physiological data.

14. A method for detecting strokes, comprising:
receiving input regarding an impaired functionality experienced by the patient;
selecting one or more of a plurality of electrodes in a sensor array at brain locations of the patient associated with the impaired functionality;
generating passive physiological analysis results by:
obtaining passive physiological data from a patient with the selected one or more of the plurality of electrodes, the passive physiological data comprising physiological data obtained while the patient remains passive;
comparing the passive physiological data with passive reference data, the passive reference data received from one or more of the plurality of electrodes at brain locations other than those associated with the impaired functionality; and
generating active physiological analysis results by:
providing a prompt for the patient to perform one or more actions;
receiving active physiological data from the selected one or more of the plurality of electrodes, the active physiological data comprising physiological data obtained while the patient attempts to perform the one or more actions; and
comparing the active physiological data with active reference data, the active reference data received from one or more of the plurality of electrodes at brain locations other than those associated with the impaired functionality; and
based on the passive physiological analysis results and the active physiological analysis results, providing a patient stroke indicator.

15. The method of claim 14, wherein obtaining passive physiological data from the patient comprises obtaining brain activity data with at least one of: an EEG array, an MEG array, an fMRI device, a PET scanner, or a CT scanner.

16. The method of claim 14, further comprising obtaining additional physiological data from the patient with one or more additional sensor devices, including at least one of: an accelerometer, a near-infrared sensor, an ultrasound sensor, a heart rate monitor, a blood pressure monitor, a respiration monitor, an electromyography (EMG) sensor, an electrocardiography (ECG) sensor, a galvanic skin sensor, a thermometer, or a camera.

17. The method of claim 16, further comprising:
comparing the additional physiological data with additional reference data; and
based on the comparison, providing a patient stroke indicator.

18. The method of claim 14, wherein the passive physiological data comprises brain activity data from a first brain hemisphere of the patient, and wherein the passive reference data comprises brain activity data from a second brain hemisphere of the patient.

19. The method of claim 14, wherein the passive reference data further comprises non-patient physiological data.

20. The method of claim 14, wherein the one or more actions comprises at least one of: lifting a limb, moving a hand or fingers, speaking, or smiling.

\* \* \* \* \*